(12) United States Patent
Mori et al.

(10) Patent No.: US 7,163,379 B2
(45) Date of Patent: Jan. 16, 2007

(54) GRADIENT LIQUID FEED PUMP SYSTEM, AND LIQUID CHROMATOGRAPH

(75) Inventors: Kiyotoshi Mori, Hitachinaka (JP); Kenichiro Takahashi, Naka-gun (JP); Masanori Takaki, Hitachinaka (JP); Masato Fukuda, Mito (JP); Masahito Ito, Hitachinaka (JP); Hironori Kaji, Hitachinaka (JP)

(73) Assignees: Hitachi High-Technologies Corporation, Tokyo (JP); Hitachi Science Systems, Ltd., Hitachinaka ( * ) Notice: Subject to any disclaimer, the term of this patent is extended or adjusted under 35 U.S.C. 154(b) by 100 days.

(21) Appl. No.: 10/504,880

(22) PCT Filed: Mar. 17, 2003

(86) PCT No.: PCT/JP03/03159

§ 371 (c)(1),
(2), (4) Date: Aug. 17, 2004

(87) PCT Pub. No.: WO03/079000

PCT Pub. Date: Sep. 25, 2003

(65) Prior Publication Data

US 2005/0084386 A1   Apr. 21, 2005

(30) Foreign Application Priority Data

Mar. 18, 2002   (JP) .............................. 2002-074781

(51) Int. Cl.
*F04B 41/06* (2006.01)

(52) U.S. Cl. ......................................................... 417/6

(58) Field of Classification Search .................... 417/4, 417/5
See application file for complete search history.

(56) References Cited

U.S. PATENT DOCUMENTS 5,664,937 A * 9/1997 Takahashi et al. ............ 417/22
5,852,231 A * 12/1998 Kaji .......................... 73/61.56

FOREIGN PATENT DOCUMENTS

| JP | 63-212778 | 9/1988 |
| JP | 64-88361 | 4/1989 |
| JP | 2-91485 | 3/1990 |

* cited by examiner

*Primary Examiner*—Anthony D. Stashick
*Assistant Examiner*—Samuel E. Belt
(74) *Attorney, Agent, or Firm*—Dickstein Shapiro LLP (57) ABSTRACT

A gradient liquid feed pump system capable of liquid feed in a correct mixing ratio even in the case of liquid feed in which the mixing ratio varies. Specifically, it comprises a first plunger pump for sucking and delivering an eluate, a second the first and second plunger pumps through a cam, a first pressure sensor for measuring the pressure in the flow path of the second plunger pump, a second pressure sensor for measuring the pressure in the fist plunger pump, a cam position detecting sensor for detecting the cam position, wherein when the cam position is in a delivery interval, the rotary speed of the motor is increased, and the period for decreasing the rotary speed is determined on the basis of the difference between the pressure values obtained from the first and second pressure sensors, respectively. Thereby, liquid feed can be smoothly effected with correct mixing ratio while avoiding pressure interference between pumps.

7 Claims, 8 Drawing Sheets

| analysis number | retention time (min) | | |
|---|---|---|---|
| No. | MPB | EPB | PPB |
| 1 | 2.626 | 4.04 | 5.98 |
| 2 | 2.626 | 4.04 | 5.98 |
| 3 | 2.626 | 4.04 | 5.98 |
| 4 | 2.626 | 4.04 | 5.98 |
| 5 | 2.626 | 4.04 | 5.98 |
| 6 | 2.626 | 4.04 | 5.98 |
| 7 | 2.626 | 4.04 | 5.973 |
| 8 | 2.626 | 4.04 | 5.973 |
| 9 | 2.626 | 4.046 | 5.98 |
| 10 | 2.626 | 4.046 | 5.98 |
| average retention time | 2.626 | 4.0412 | 5.9786 |
| SD | 0 | 0.00253 | 0.002951 |
| RSD% | 0 | 0.062601 | 0.049367 |

FIG. 7B

| analysis number | retention time (min) | | |
|---|---|---|---|
| No. | MPB | EPB | PPB |
| 1 | 2.619 | 4.033 | 5.973 |
| 2 | 2.626 | 4.04 | 5.973 |
| 3 | 2.623 | 4.033 | 5.98 |
| 4 | 2.626 | 4.04 | 5.98 |
| 5 | 2.633 | 4.04 | 5.987 |
| 6 | 2.633 | 4.033 | 5.98 |
| 7 | 2.626 | 4.033 | 5.973 |
| 8 | 2.626 | 4.04 | 5.973 |
| 9 | 2.626 | 4.046 | 5.987 |
| 10 | 2.626 | 4.046 | 5.987 |
| average retention time | 2.6264 | 4.0384 | 5.9793 |
| SD | 0.004142 | 0.00519 | 0.006129 |
| RSD% | 0.157704 | 0.12851 | 0.102506 |

FIG. 8

GRADIENT LIQUID FEED PUMP SYSTEM, AND LIQUID CHROMATOGRAPH

TECHNICAL FIELD

The present invention relates to a pump for executing gradient liquid feed, and in particular to a pump for use in a liquid chromatograph for executing high-pressure gradient liquid feed.

BACKGROUND ART

With a high-pressure gradient liquid chromatograph for executing analysis while varying a mixing ratio of eluants fed into a separation column, a plurality of the eluants are fed by different pumps, respectively. In the case of using a plunger pump provided with check valves, executing liquid feed by the reciprocating motion of a piston, for each of the pumps, there occurs time periods when pressure drop develops on the side of one of the pumps, adjacent to the separation column, (on the delivery side of the pump), due to the constitution thereof. Such pressure drop is introduced to the liquid feed of the other pump, resulting in so-called pressure interference between the pumps, so that the liquid feed at a flow rate according to a program is hindered, causing a problem that the mixing ratio of the eluants undergoes variation.

Countermeasures against the pressure interference have been disclosed in, for example, JP-A No. 15245/1996, JP-A No. 50967/1999, and JP-A No. 72130/1995, respectively.

DISCLOSURE OF THE INVENTION

With a conventional pump system using plunger pumps, when pressure drop starts upon the pump falling in a delivery interval, the rotational speed of a motor for controlling the reciprocating motion of the plunger of the plunger pump through the intermediary of a cam is increased, thereby attempting to shorten an interval of such a pressure drop. As to until when the rotational speed of the motor is kept increased, however, various methods have been tried.

For example, in JP-A No. 15245/1996, it is described that a pressure value on the delivery side of a pump is detected, and the rotational speed of a motor is increased upon the start of pressure drop while the motor is caused to revert to the steady-state rotational speed thereof similarly upon the pressure value on the delivery side of the pump reverting to a predetermined pressure value. Further, according to JP-A No. 50967/1999, time to increase the rotational speed of a motor is decided upon depending on the position of a cam, and the motor is caused to revert to the steady-state rotational speed thereof at a point in time with the passage of a predetermined time.

With the pump system using the plunger pumps, pressure drop causing the pressure interference occurs in a time period during which the plunger pump having check valves undergo transition from a suction interval to a delivery interval. In the case of flow rates in the respective plunger pumps varying by the moment, the time period during which the pressure interference occurs vary by the plunger pump, so that it is difficult to correctly predict a time band in which the pressure interference occurs.

In order to reduce occurrence of the pressure interference, it is necessary to reduce variation in the flow rates of liquids delivered by the respective plunger pumps. To that end, it is necessary to grasp the extent to which the flow rates (pressures) of liquids that are about to be delivered by the respective plunger pumps differ from pressures in flow paths on the delivery sides of the respective plunger pumps. Time when the pressures undergo variation corresponds to the case where the motor is operated at a high speed as described above, however, in the conventional case, timing to complete a high-speed operation of the motor is based only on the pressures in the flow paths on the delivery sides of the respective plunger pumps, as determination criteria, or based on a predetermined time, and consequently, delivery pressures in the respective plunger pumps themselves are not included in the determination criteria. For this reason, there have been cases where the delivery pressure is found too high or too low, depending on timing for completing the high-speed operation of the motor, so that it has been impossible to execute the liquid feed at a stable pressure.

It is therefore an object of the invention to provide a gradient liquid feed pump system capable of liquid feed at a correct mixing ratio by reducing the effect of pressure interference even in the case of flow rates in respective pumps varying by the moment, and a liquid chromatograph using the gradient liquid feed pump system.

To that end, the invention provides a gradient liquid feed pump system capable of feeding liquid while varying a mixing ratio of a plurality of eluants by use of a plurality of pumps, said pumps each comprising a first plunger pump for sucking and delivering the eluant, a second plunger pump for receiving the eluant fed from the first plunger pump, and executing the suction and delivery thereof, a motor for driving the first and second plunger pumps through a cam, a first pressure sensor for measuring pressure in the flow path of the second plunger pump, a second pressure sensor for measuring pressure in the first plunger pump, and a cam position detecting sensor for detecting a cam position; wherein the rotational speed of the motor is increased when the cam position falls in a delivery interval, and a period for decreasing the rotational speed of the motor is determined on the basis of a difference between pressure values obtained from the first and second pressure sensors, respectively.

As a result, it becomes possible to execute the liquid feed at a stable mixing ratio of the eluants.

BEST MODE FOR CARRYING OUT THE INVENTION

Embodiments of the invention are described hereinafter.

Figure 1:
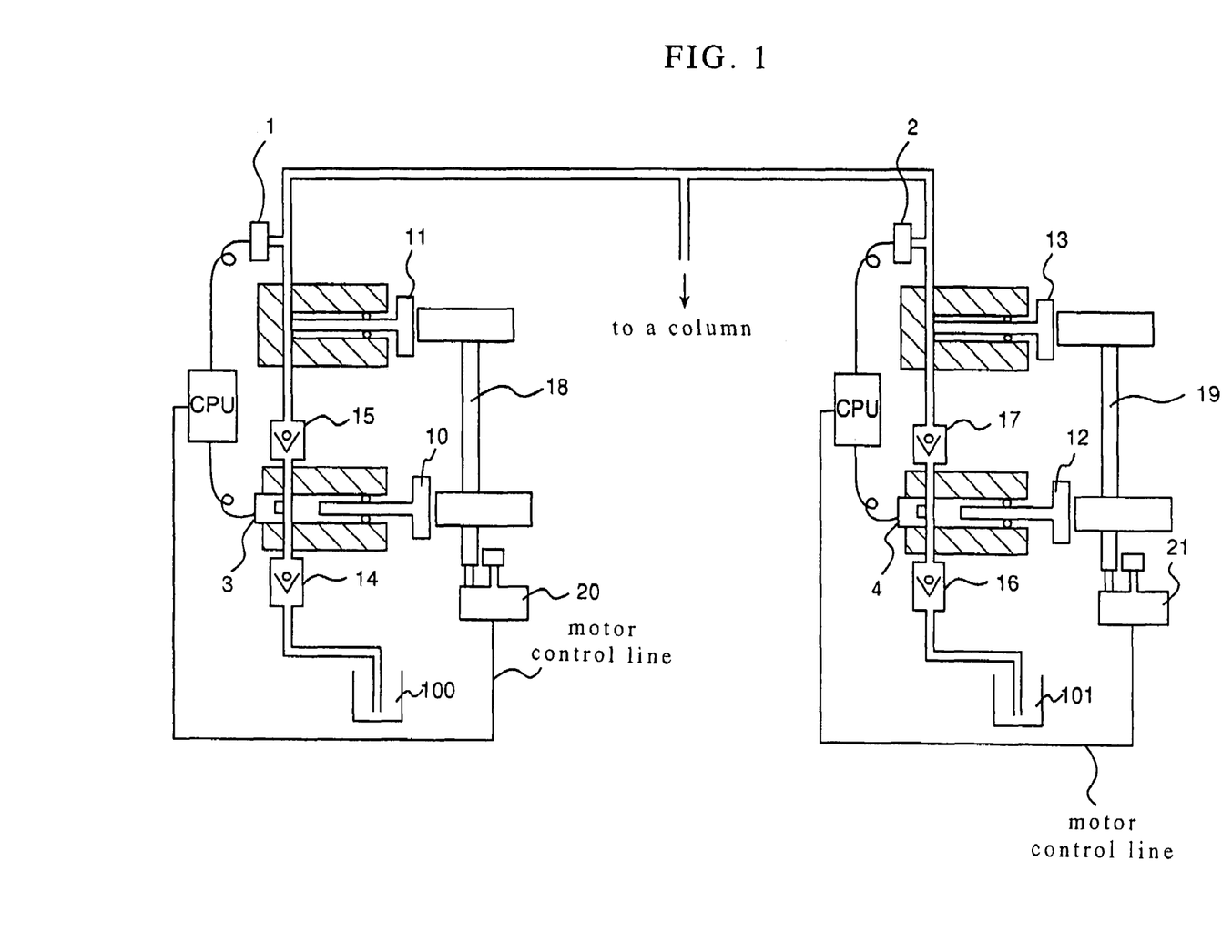
FIG. 1 is a schematic block diagram of an embodiment of the invention.

FIG. 1 is a schematic block diagram of an embodiment of a high-pressure gradient elution pump system according to the invention, comprising two units of pumps. The respective pumps are provided with two pump chambers, and motors (preferably, pulse motors) 20, 21 drive respective pistons of the pump chambers through cams 18, 19, respectively. The pump chambers on the sides of the respective pumps, adjacent to eluants 100, 101, respectively, are provided with a pair of check valves for prevention of reverse flow, on the delivery and suction sides thereof, respectively, and liquid feed is effected by first pistons 10, 12, respectively, while the pump chambers on the sides of the respective pumps, adjacent to a separation column, are not provided with a check valve, effecting liquid feed by second pistons 11, 13, respectively.

The second pistons 11, 13 each deliver liquid in an interval when the first pistons 10, 12 each are in a suction interval. During this time period, the check valves 14, 16, on the suction sides of the respective pumps, respectively, are open, and the check valves 15, 17, on the delivery sides thereof, respectively, are closed. Further, in respective suction intervals of the second pistons 11, 13, the first pistons 10, 12 each deliver the liquid in amounts greater than respective suction flow rates of the second pistons 11, 13, thereby keeping respective total delivery flow rates of the liquid from the respective pumps at a constant rate. During this time period, the check valves 14, 16 on the suction sides, respectively, are closed, and the check valves 15, 17, on the delivery sides, respectively, are open.

With the present embodiment, the respective pumps, one unit each, are provided with two types of pressure sensors, that is, pressure sensors 3, 4, for measuring pressure inside the respective pump chambers with the check valves, on the respective suction sides, and pressure sensors 1, 2, for measuring pressure in respective flow paths on the respective delivery sides. In the case of the system shown in FIG. 1, the total number of the pressure sensors is four. In a basic state, the former pressure sensors 3, 4 each have a pressure value substantially at 0 in the respective suction intervals, indicating a pressure value substantially equal to that of the latter pressure sensors 1, 2, respectively, in the respective delivery intervals. Further, cam position detecting sensors (not shown) for detecting respective rotation angles of the cams 18, 19 are provided to thereby keep track of cam positions all the time.

Figure 2:
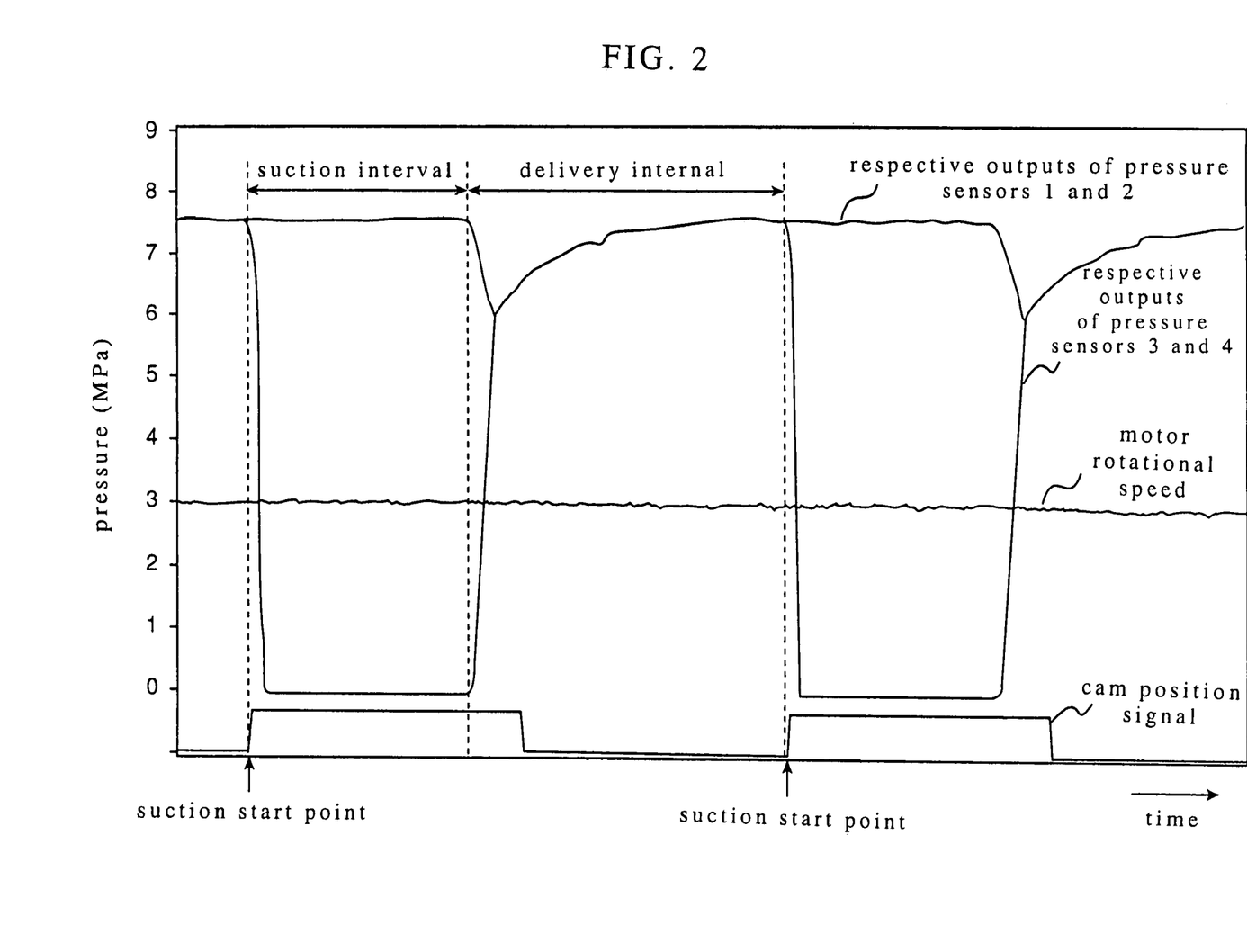
FIG. 2 is a graph showing variation in outputs of respective pressure sensors, a rotational speed of each of motors, and cam position signals, in the case of rotating the motors at a given speed.

FIG. 2 is a graph showing outputs of the respective pressure sensors in the case of rotating the motors 20, 21 at a given speed {in the case of the present embodiment, rotated at 160 pps (pulse per second) provided rotated at a rate of 0.075 deg/1 pulse}. In the graph, rotational speeds of the motors 20, 21, together with respective cam position signals for the cams 18, 19, are shown in addition to pressures. With the cam position signal, the rising edge thereof shows the start point of the suction interval, indicating that the cam undergoes one rotation in one cycle. In general, a cam position in a range of 0° to 120° corresponds to the suction interval while the same in a range of 120° to 360° corresponds to the delivery interval. In the case of the present embodiment shown in FIG. 2, since the motors 20, 21 are rotated at the given speed, a sharp pressure drop occurs to the respective pressures of the pressure sensors 1, 2 at the start point of the delivery interval. As a result of such a sharp pressure drop occurring to each of the pumps, this has an effect on the other pump.

Figure 3:
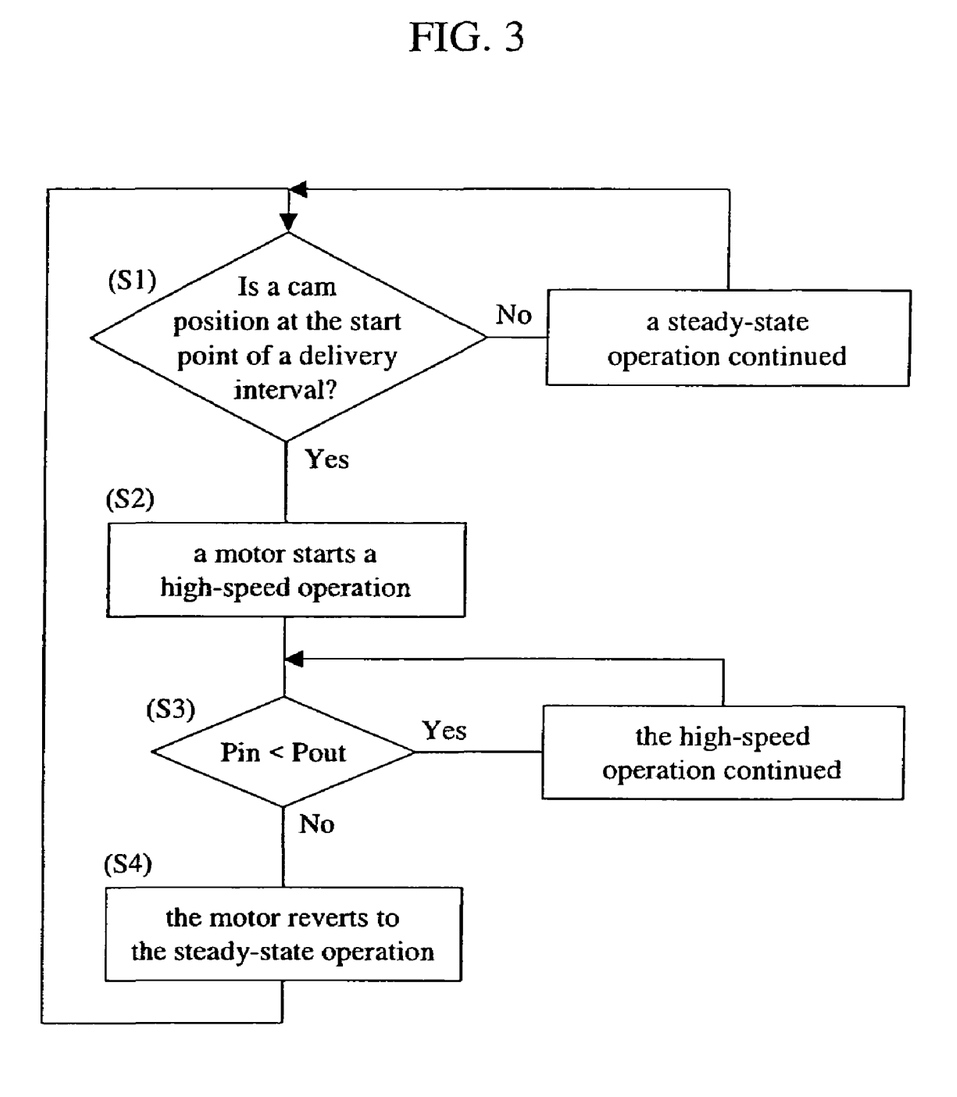
FIG. 3 is a flow chart showing an operation algorithm according to the invention.

With the present embodiment, for each of the pumps, pressure inside the pump chamber on the suction side thereof, and pressure in the flow path on the delivery side thereof are detected, whereupon a CPU executes calculation on the basis of respective pressure values, thereby issuing a control instruction to the motor. FIG. 3 shows an operation algorithm.

First, the cam position is detected to thereby determine whether or not the cam has reached the start point of the delivery interval (a step S1). During a time period when the cam position falls short of the start point of the delivery interval, the motor continues an operation at the steady-state rotational speed. Upon the cam position reaching the start point of the delivery interval, the motor starts a high-speed operation (a step S2) to thereby determine whether or not pressure Pin of the pressure sensor 3 or 4 has become equivalent to pressure Pout of the pressure sensor 1 or 2 (a step S3). As long as a state of Pin<Pout remains, the motor continues the high-speed operation. The high-speed operation is preferably continued at a speed twice as fast as a normal rotational speed. Upon elimination of a difference between Pin and Pout, the motor reverts to the operation at the steady-state rotational speed (a step S4). Thereafter, the operation is repeated by starting from the step S1 again.

Figure 4:
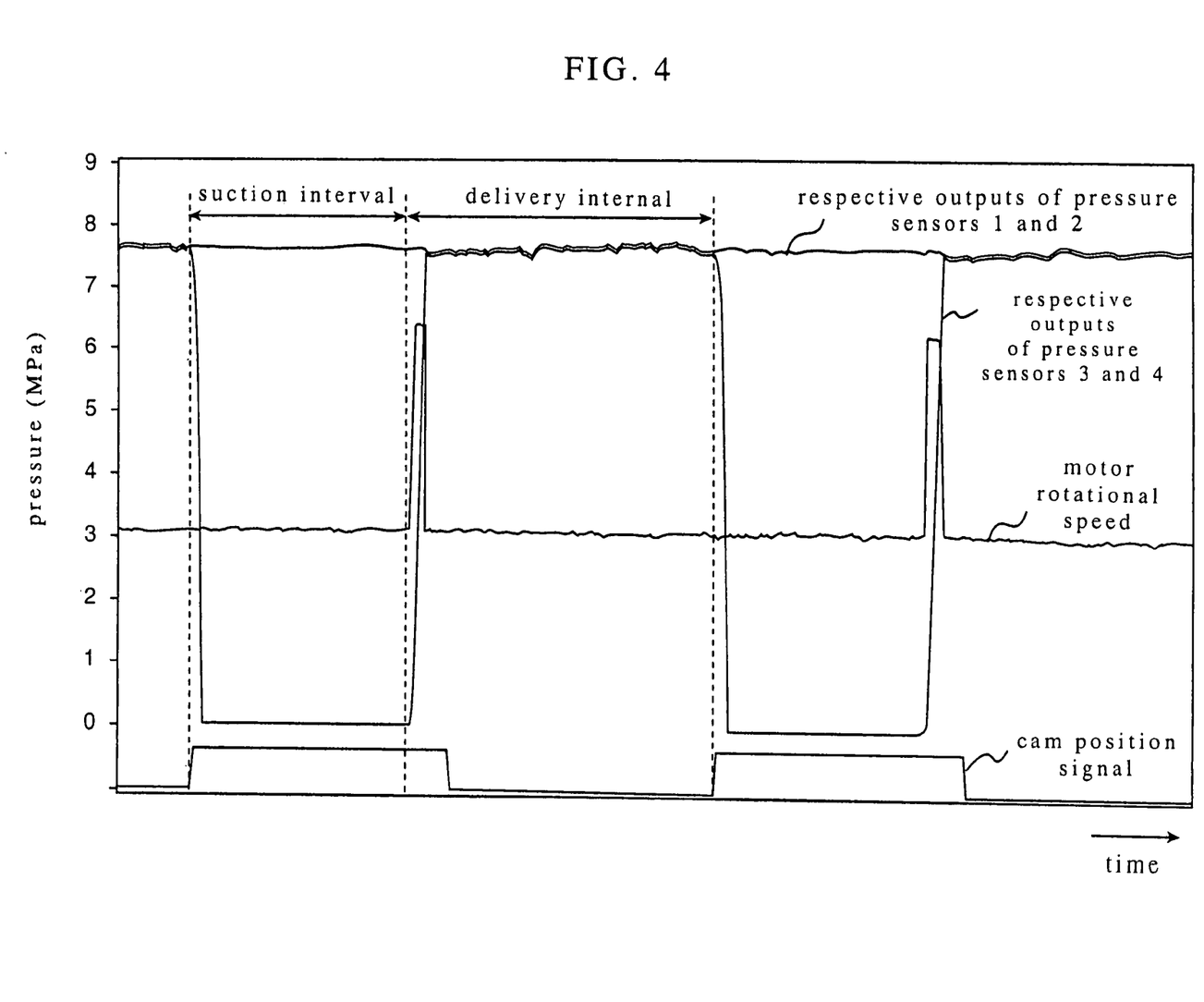
FIG. 4 is a graph showing variation in outputs of the respective pressure sensors, the rotational speed of each of the motors, and the cam position signals at a time when the invention is carried out.

That is, with the present embodiment, control is executed such that the pressure value in the flow path on the delivery side is used as a target value, and the motor is caused to continue the high-speed operation until the pressure inside the pump chamber on the suction side reach the target value. FIG. 4 shows results of the outputs of the respective pressure sensors, obtained by the control of the present embodiment. As shown in FIG. 4, the rotational speed of each of the motors in the delivery interval is seen as a speed twice as fast as in a normal case (in the case of the present embodiment shown in FIG. 4, the speed is increased up to 320 pps). Pressure drop in the respective outputs of the pressure sensors 1 and 2 is hardly observed.

Figure 5:
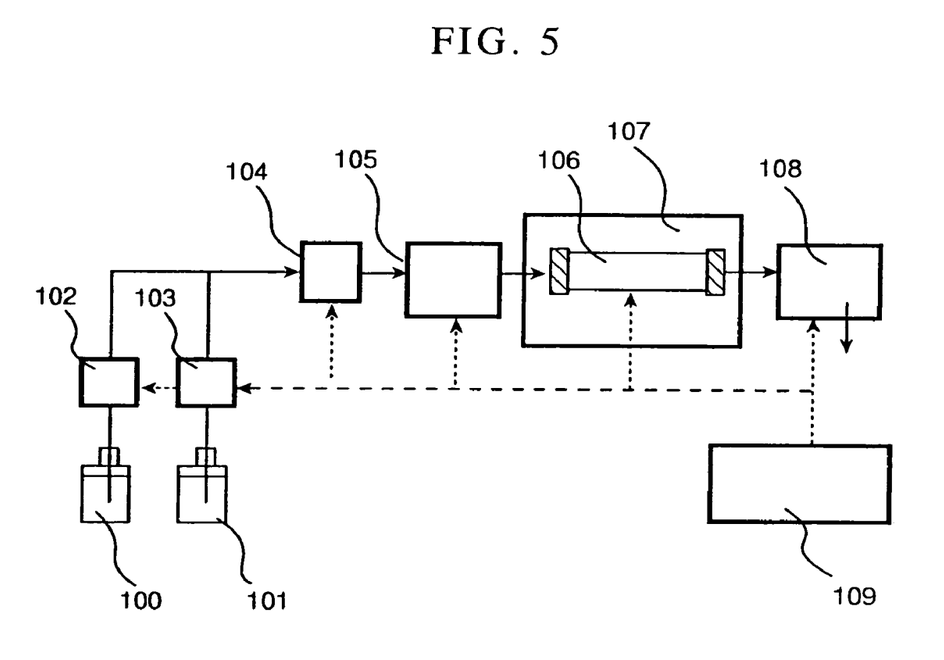
FIG. 5 is a schematic block diagram of a liquid chromatograph to which the pump system according to the invention is applied.

FIG. 5 shows an example of a high-pressure gradient liquid chromatograph to which the pump system according to the present embodiment of the invention is applied. The eluants 100, 101 are fed by pumps 102, 103, respectively, while mixture composition thereof is varied over the course of time. Thereafter, the eluants 100, 101 are agitated by a mixer 104, and subsequently, a sample to be analyzed is added to the eluants by an injector inside an auto-sampler 105. The eluants with the sample added thereto are guided into a separation column 106. In order to execute separation of multiple components with high reproducibility, the separation column 106 is installed in a column oven 107 kept at a given temperature. Respective components separated by the separation column 106 are detected by a detector 108, and detection data are processed by, and stored in a data processor 109. Further, the data processor 109 normally executes control of respective parts. With the present embodiment, an ODS column is used for the separation column 106, and a UV detector is used for the detector 108.

Figure 6:
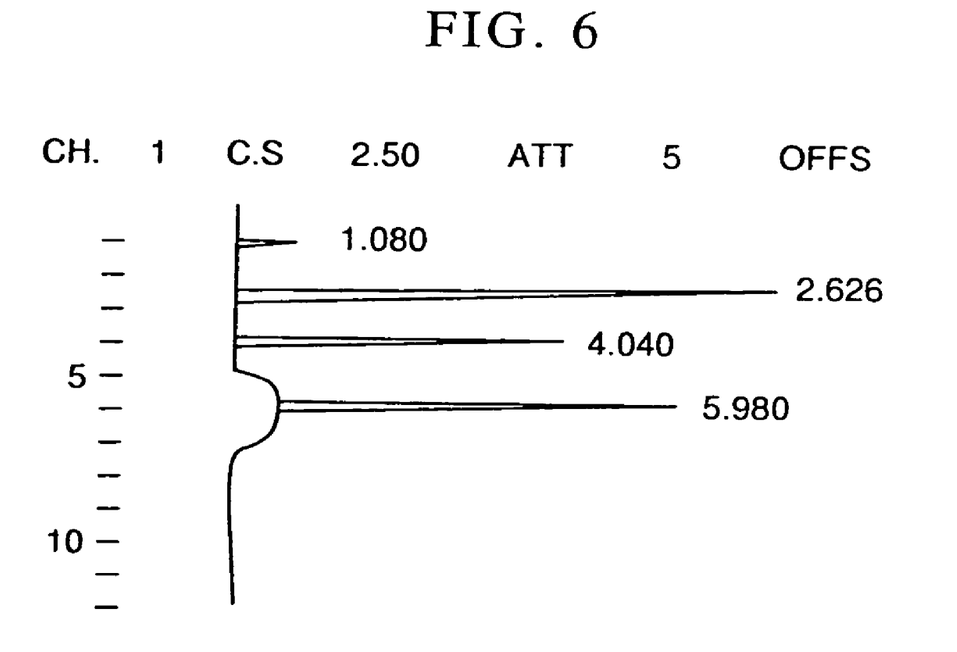
FIG. 6 is a view showing an example of a chromatogram obtained by an apparatus shown in FIG. 5.
Figure 7A:
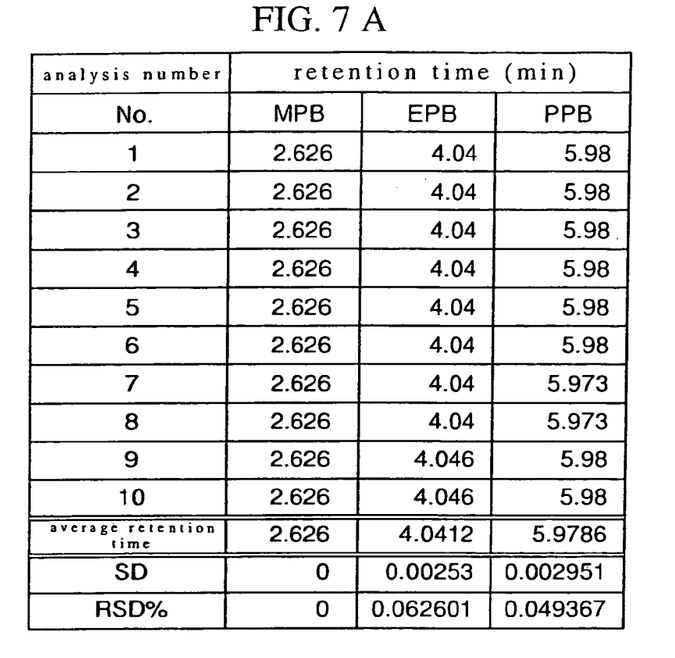
FIG. 7A is a view showing the results of measurements repeated 10 times by use of the embodiment of the invention.

FIG. 6 shows a chromatogram obtained by injecting a standard sample, containing three components of MPB, EPB, and PPB, into such an apparatus as described. In the chromatogram shown in FIG. 6, a peak at retention time of 2.626 (min) represents MPB, a peak at retention time of 4.040 (min) EPB, and a peak at retention time of 5.980 (min) PPB. Table in FIG. 7A shows the retention times of the respective components when the chromatograms were obtained by repeating measurements 10 times. Average retention time, SD (standard deviation), and RSD (relative standard deviation) were found for each of the components, to thereby check the extent of variations.

Figure 7B:
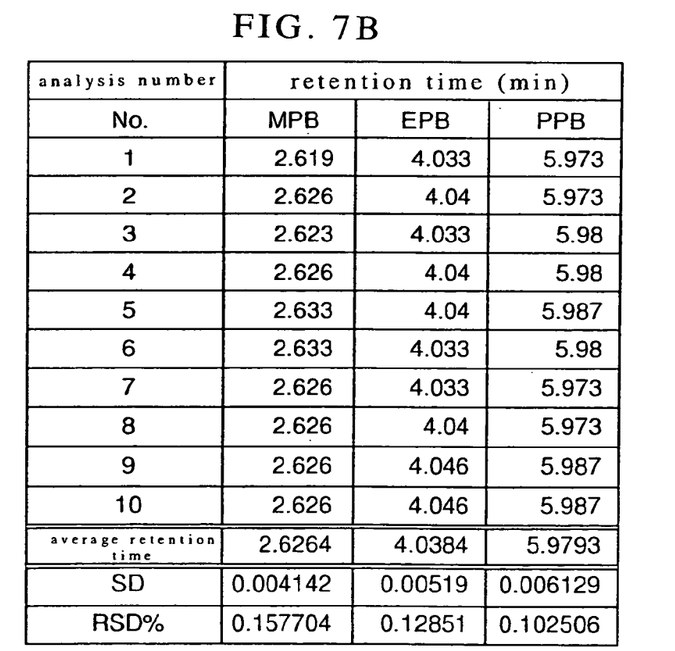
FIG. 7B is a view showing the results of measurements of the same sample as one in the case of FIG. 7A, repeated 10 times by use of a conventional apparatus.

In contrast, FIG. 7B shows the results of measuring 10 times the standard sample, containing the three components of MPB, EPB, and PPB, similarly to the above-described case, in the case where the high-speed operations of the respective motors are executed by use of only the respective outputs of the pressure sensors 1, 2, in the respective flow paths on the respective delivery sides, as triggers, without the use of the respective outputs of the pressure sensors 3, 4, inside the pump chambers on the respective suction sides (that is, control is executed such that the high-speed operations of the respective motors are started upon the occurrence of pressure drop to the respective outputs of the pressure sensors 1, 2, and the motor reverts to the operation at the steady-state rotational speed when the respective outputs of the pressure sensors 1, 2 are restored) as with case of the conventional apparatus.

Comparison of RSDs shows that about 0.063% is obtained for EPB in FIG. 7A while about 0.129% is obtained for EPB in FIG. 7B, indicating that with the apparatus according to the present embodiment, variations in the retention time became smaller as compared with those for the conventional apparatus, and stable gradient elution was implemented. The cause for an increase in the variations of the retention time in FIG. 7B is that, with the conventional apparatus, timing to start and complete the high-speed operation of each of the motors is dependent only on the pressure in the flow path on the delivery side thereof, so that a delivery flow rate underwent variation by the effect of pressure interference due to pressure drop occurring to the other pump.

In contrast, with the present embodiment, the start point of the high-speed operation of the motor is determined on basis of the cam position, and the completion point thereof is determined by checking a difference between the pressure in the flow path on the delivery side, and the pressure inside the pump chamber on the suction side, so that the pump on one side is capable of feeding liquid at a stable delivery flow rate without being interfered with by variation in pressure accompanying the suction and delivery of liquid by the other pump. As a result, this will subsequently enable pressure interference affecting the other pump to be reduced, so that the pump system as a whole is capable of stable gradient elution.

Figure 8:
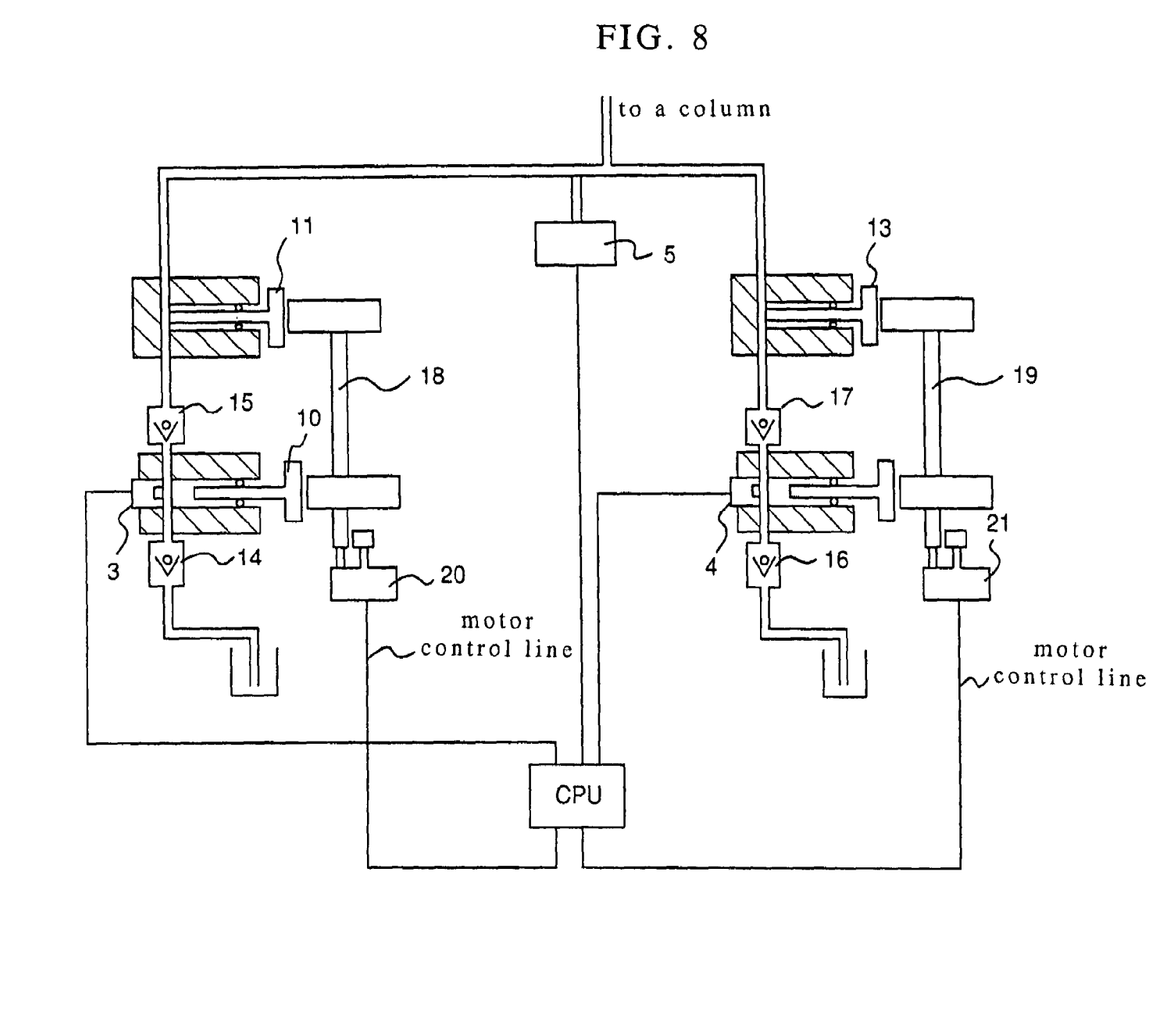
FIG. 8 is a schematic block diagram of another embodiment of the invention.

FIG. 8 shows another embodiment of the invention. It is a high-pressure gradient elution pump system, comprising two units of pumps, similar to one shown in FIG. 1, however, it differs from the latter in that three pressure sensors are used. Respective pumps are provided with pressure sensors 3, 4, for measuring pressures inside respective pump chambers on the suction sides thereof. In addition, there is provided one pressure sensor 5 for measuring pressure in flow paths on the delivery sides of the respective pumps. With the system shown in FIG. 1, the respective pumps are provided with the pressure sensor for measuring the respective pressures in the flow paths on the delivery sides thereof. With the system in FIG. 8, however, those pressure sensors shown in FIG. 1 are integrated with each other so as to serve as a common pressure sensor.

Further, in the case of the embodiment shown in FIG. 8, the system has one unit of CPU. In the case of controlling the pump having the pressure sensor 3, the CPU generally calculates respective pressure values of the pressure sensors 3, and 4, thereby issuing a control instruction to a motor 20 of one of the pumps. With the present embodiment, an operation algorithm is basically the same as the operation algorithm for the embodiment shown in FIG. 1 accept that the output of the pressure sensor 5 is used for the pressure Pout in the flow path on the delivery side, to be used when determining the completion of a high-speed operation, in respect of either of the pumps. That is, until the output of the pressure sensor 3 becomes equal to the output of the pressure sensor 5, the motor 20 continues the high-speed operation. The high-speed operation is preferably continued at a speed twice as fast as the normal rotational speed. In the case of controlling the pump having the pressure sensor 4, the CPU similarly calculates respective pressure values of the pressure sensors 3, and 4, thereby issuing a control instruction to a motor 21 of the other pump.

With the respective embodiments described in the foregoing, a case of using two units of the pumps is described; however, it is to be pointed out that the system comprising not less than three units of pumps is capable of gradient control.

With the invention, in order to prevent pressure drop from occurring in a period of transition of the piston in the pump chamber on the suction side of the pump from the suction interval to the delivery interval, the pressure sensor is installed in the pump chamber on the suction side, the motor for driving the piston is caused to start the high-speed operation upon checking the arrival of the piston at the delivery interval on the basis of the cam position, and further, the high-speed operation of the motor is continued until the pressure in the pump chamber on the suction side rises rapidly up to the pressure value(s) of the pressure sensor(s) installed in the flow path(s) on the delivery side of the pump, thereby rendering the pump insusceptible to the pressure interference by the other pump, so that the system is capable of feeding liquid at a stable flow rate.

With the invention described hereinbefore, liquid feed can be effected at a stable mixing ratio of the eluants. Consequently, if the invention is applied to a liquid chromatograph, a detection base line signal is stabilized, and detection noises can be reduced, thereby enhancing a detection limit. Further, the invention will contribute to stabilization of the respective retention times of analyzed components retained in the separation column.

The invention claimed is:
1. A gradient liquid feed pump system capable of feeding liquid while varying a mixing ratio of a plurality of eluants by use of a plurality of pumps, said pumps each comprising:
   a first plunger pump for sucking and delivering the eluant;
   a second plunger pump for receiving the eluant fed from the first plunger pump, and executing the suction and delivery thereof;
   a motor for driving the first and second plunger pumps through a cam;
   a first pressure sensor for measuring pressure in the flow path of the second plunger pump;
   a second pressure sensor for measuring pressure in the first plunger pump;
   a cam position detecting sensor for detecting a cam position; and
   a control means for issuing a control instruction to the motor,
   wherein the control means increases the rotational speed of the motor when the cam position falls in a delivery interval, and determines a period for decreasing the rotational speed of the motor on the basis of a differ- ence between pressure values obtained from the first and second pressure sensors, respectively.

2. A gradient liquid feed pump system according to claim 1, wherein:
the first and second plunger pumps are for executing suction and delivery by the reciprocating motion of a piston, respectively,
the first plunger pump has a pair of check valves for prevention of reverse flow, provided on the delivery and the suction sides of the piston, respectively, and
the second pressure sensor measures pressure between the check valves.

3. A gradient liquid feed pump system according to claim 1, wherein the rotational speed of the motor is increased up to a speed twice as fast as that in a suction interval when the rotational speed of the motor is increased.

4. A gradient liquid feed pump system capable of liquid feed after executing the suction and delivery of a plurality of eluants by use of respective pumps, and mixing the eluants, having a first pressure sensor provided in a flow path through which solutions delivered from the respective pumps pass, said respective pumps comprising:
a first plunger pump for sucking and delivering the eluant;
a second plunger pump for receiving the eluant fed from the first plunger pump and executing the suction and delivery thereof;
a motor for driving the first and second plunger pumps through a cam;
a second pressure sensor for measuring pressure in the first plunger pump; and
a cam position detecting sensor for detecting a cam position; and
a control means for issuing a control instruction to the motor,
wherein the control means increases the rotational speed of the motor when the cam position falls in a delivery interval, and determines a period for decreasing the rotational speed of the motor on the basis of a difference between pressure values obtained from the first and second pressure sensors, respectively.

5. A gradient liquid feed pump system according to claim 4, wherein:
the first and second plunger pumps are for executing suction and delivery by the reciprocating motion of a piston, respectively,
the first plunger pump has a pair of check valves for prevention of reverse flow, provided on the delivery and the suction sides of the piston, respectively, and
the second pressure sensor measures pressure between the check valves.

6. A gradient liquid feed pump system according to claim 4, wherein the rotational speed of the motor is increased up to a speed twice as fast as that in a suction interval when the rotational speed of the motor is increased.

7. A liquid chromatograph comprising a pump system capable of liquid feed while varying a mixing ratio of a plurality of eluants by use of a plurality of pumps, a sample feeder for guiding a sample into the eluants, a separation column for executing separation of the sample and a detector for detecting solutions eluted from the separation column, said pump system having a first pressure sensor for measuring pressure in a flow path on the side thereof, adjacent to the sample feeder, and the respective pumps in said pump system being provided with check valves for prevention of reverse flow, said respective pumps comprising:
a first plunger pump for sucking and delivering the eluant;
a second plunger pump for receiving the eluant fed from the first plunger pump and executing the suction and delivery thereof;
a motor for driving the first and second plunger pumps through a cam;
a second pressure sensor for measuring pressure in the first plunger pump; and
a cam position detecting sensor for detecting a cam position; and
a control means for issuing a control instruction to the motor,
wherein the control means increases the rotational speed of the motor when the cam position falls in a delivery interval, and determines a period for decreasing the rotational speed of the motor on the basis of a difference between pressure values obtained from the first and second pressure sensors, respectively.

* * * * *